(12) United States Patent
Clark

(10) Patent No.: US 7,628,489 B2
(45) Date of Patent: Dec. 8, 2009

(54) VISUAL AXIS AND ALIGNMENT MEASUREMENT SYSTEM AND METHOD OF USING SAME

(76) Inventor: Thomas H. Clark, 149 Mallard Dr., Colchester, VT (US) 05446

( * ) Notice: Subject to any disclaimer, the term of this patent is extended or adjusted under 35 U.S.C. 154(b) by 237 days.

(21) Appl. No.: 11/676,497

(22) Filed: Feb. 19, 2007

(65) Prior Publication Data

US 2007/0285620 A1    Dec. 13, 2007

Related U.S. Application Data

(60) Provisional application No. 60/804,371, filed on Jun. 9, 2006.

(51) Int. Cl.
*A61B 3/10* (2006.01)
(52) U.S. Cl. .................. 351/211; 351/204; 351/214
(58) Field of Classification Search ................. 351/211, 351/214, 204
See application file for complete search history.

(56) References Cited

U.S. PATENT DOCUMENTS

| | | | | |
|---|---|---|---|---|
| 4,252,419 A | * | 2/1981 | Padula et al. | 351/204 |
| 4,381,143 A | * | 4/1983 | Bommarito | 351/230 |
| 4,531,297 A | * | 7/1985 | Stoerr | 33/200 |
| 5,237,351 A | * | 8/1993 | Kohayakawa et al. | 351/243 |

\* cited by examiner

*Primary Examiner*—Jordan M. Schwartz
*Assistant Examiner*—James C Jones

(57) ABSTRACT

A visual axis and alignment measurement system and method of using same are disclosed. In particular, a visual axis measurement system of the present disclosure includes a visual axis measurement device and a near point target. The visual axis measurement device includes a pair of opaque lenses, each having a slit therein, that are adjustably coupled via a coupling mechanism. The visual axis measurement device also includes a linear measurement device. Via self-adjustment, the patient may align the respective slits for his/her dominant and non-dominant eyes along his/her visual axes until the near point target is in focus. After which, the distance between the centers of the slits is measured in order to determine accurately the placement of bifocal lens segments within eyeglass lenses. In doing so, it is ensured that the prescription for, for example, progressive bifocal corrective lenses, which have narrow viewing areas, is correct.

16 Claims, 6 Drawing Sheets

VISUAL AXIS AND ALIGNMENT MEASUREMENT SYSTEM AND METHOD OF USING SAME

RELATED APPLICATION DATA

This application claims the benefit of priority of U.S. Provisional Patent Application Ser. No. 60/804,371 filed Jun. 9, 2006, and titled "Visual angle and alignment measuring device," that is incorporated by reference herein in its entirety.

FIELD OF THE DISCLOSURE

The present disclosure generally relates to a visual axis measurement apparatus. In particular, the present disclosure is directed to a visual axis and alignment measurement system for determining accurately the placement of bifocal segments within progressive bifocal corrective lenses.

BACKGROUND

Opticianry is the professional practice of filling prescriptions for ophthalmic lenses and dispensing eyeglasses. When fitting progressive bifocals, the placement of the bifocal lens segment within the eyeglass lens should be such that the subject's gaze is centered through the bifocal lens when the subject is in a reading position, which is when the subject is holding his/her reading material about 300-500 millimeters (mm) away. Longstanding and current measuring techniques for determining the placement of bifocal lens segments within eyeglass lenses include physically measuring the distance between the optical axes of the patient's eyes, which is the distance between the centers of the pupils.

However, in a significant percent (e.g., about 25%) of bifocal wearers, the optical (pupillary) axis measurement produces an incorrect alignment because the optical (pupillary) axis of the eye is not always aligned with the visual axis of the eye. The visual axis is one's line of vision, which is a straight line that joins the fovea of the eye with a near fixation point. A consequence of using the optical (pupillary) axis measurement only for determining the placement of bifocal lens segments within eyeglass lenses is that the placement of the bifocal lens segments may not properly align with the patient's visual axis and, thus, the patient may experience blurriness and/or a noticeable degradation of the perceived binocular image. In particular, the viewing areas of progressive bifocal lenses are narrow and, thus, any slight misalignment is noticeable. As a result, the patient is dissatisfied with, for example, his/her progressive bifocal eyeglasses and further time and money is spent for return visits to the optician for follow-up corrective action.

For these reasons, a need exists for a visual axis and alignment measurement system for determining accurately the placement of bifocal lens segments within eyeglass lenses, in order to ensure that the resulting prescription for progressive bifocal corrective lenses, which have narrow viewing areas, is correct. In doing so, the time and money that is spent for return visits to the optician for follow-up corrective action because of poorly fitted progressive bifocals is reduced, as well as replacement of material.

SUMMARY OF THE DISCLOSURE

The invention provides a visual axis and alignment measurement system that includes a visual axis measurement device and a visual target. The visual target may be positioned at a distance (d1), e.g., 300 mm to about 500 mm, from, and in visual contact with the visual axis measurement device. The visual axis measurement device includes first and second opaque lens adjustably coupled to one another along an axis that runs between a patient's two eyes, first and second slits defined within the first and second opaque lens respectively, and a coupling mechanism mechanically attached to the first and second opaque lens. The coupling mechanism is used to adjust a distance (d2) between the first and second slits. The visual axis and alignment measurement system may further include a measurement device for measuring the distance (d2) between centers of the first and second slits. The measurement device may be a Standard English or metric ruler, a caliper device, or an electronic linear measurement device.

The visual axis and alignment measurement system may further include an occluder for occluding the first and/or second slit. The occluder may be mechanically coupled to the visual axis measurement device. The visual target of the visual axis and alignment measurement system may be a printed display or a video display device.

The invention further provides a method of performing a visual axis alignment and measurement, including, first positioning a patient at a visual axis measurement device; then adjusting a first or second slit that is associated with the patient's dominant eye, such that the visual target at a distance (d1) is aligned with the patient's dominant eye's visual axis; next adjusting the first or second slit that is associated with the patient's non-dominant eye, such that a visual target, at a distance (d1), is aligned with the patient's non-dominant eye's visual axis; and then measuring distance (d2) between centers of the first and second slit, wherein the distance (d2) is a visual axis measurement.

The invention further provides a progressive bifocal eyeglass lens, including an eyeglass lens that further includes a bifocal lens segment integrated into said eyeglass lens, wherein the bifocal lens segment is physically aligned with a visual axis of a patient's eye as a result of using a visual axis and alignment measurement system and method.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
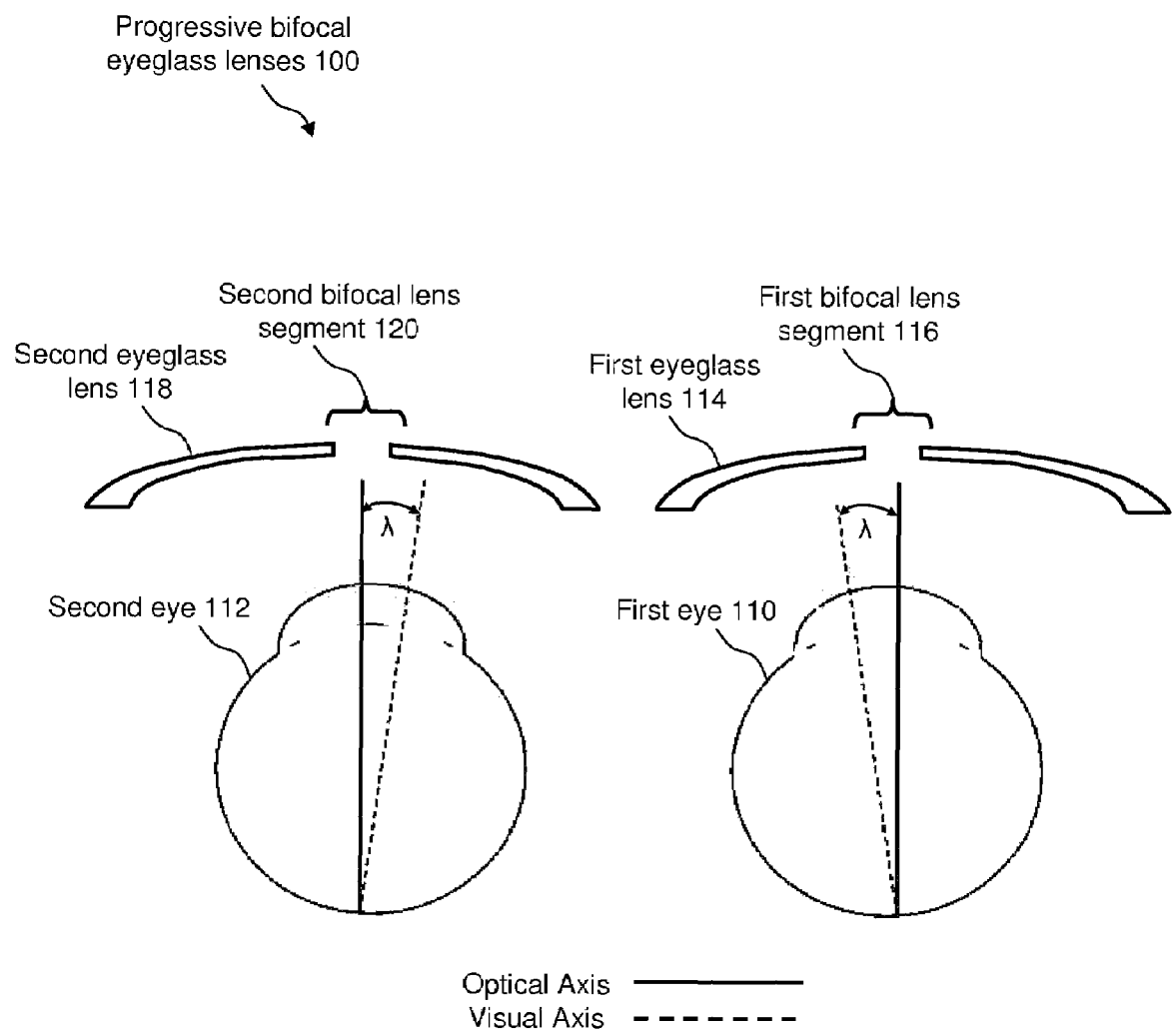
FIG. 1 illustrates a cross-sectional view of a pair of prior art progressive bifocal eyeglass lenses.

FIG. 1 illustrates a cross-sectional view of a pair of prior art progressive bifocal eyeglass lenses 100. In particular, FIG. 1 shows a first eye 110, which may be a subject's right eye that is directed toward a first eyeglass lens 114 of progressive bifocal eyeglass lenses 100. Integrated within first eyeglass lens 114 is a first bifocal lens segment 116, which is aligned physically with an optical (pupillary) axis of first eye 110. Similarly, FIG. 1 shows a second eye 112, which may be a subject's left eye that is directed toward a second eyeglass lens 118 of progressive bifocal eyeglass lenses 100. Integrated within second eyeglass lens 118 is a second bifocal lens segment 120, which is aligned physically with an optical (pupillary) axis of second eye 112. FIG. 1 illustrates that the placement of first bifocal lens segment 116 and second bifocal lens segment 120 is based on physically measuring the distance between the optical axes of first eye 110 and second eye 112.

Additionally, FIG. 1 shows that first eye 110 and second eye 112 each have a visual axis that may be misaligned with their respective optical (pupillary) axis by an angle lambda ($\lambda$). As a result, first bifocal lens segment 116 of first eyeglass lens 114 and second bifocal lens segment 120 of second eyeglass lens 118 may not align with the visual axis of first eye 110 and second eye 112, respectively. Consequently, the user of the prior art progressive bifocal eyeglass lenses 100 may experience blurriness and/or a noticeable degradation of the perceived binocular image.

Figure 2:
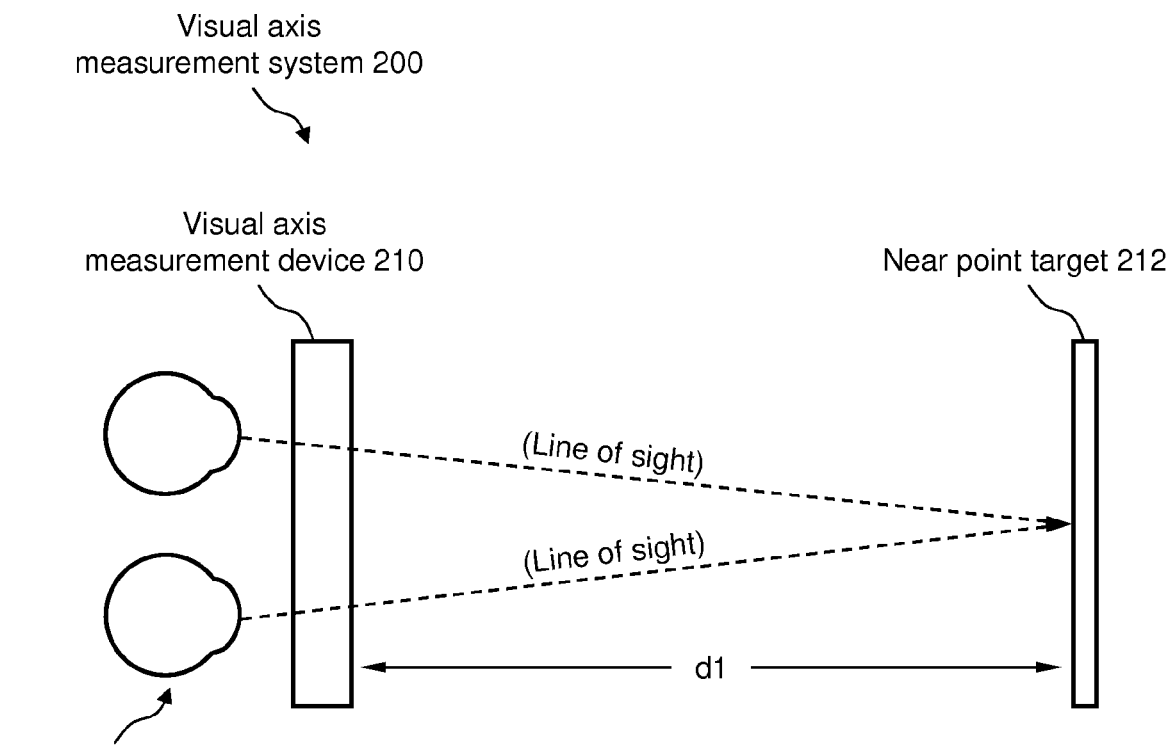
FIG. 2 illustrates a top view of a visual axis measurement system in accordance with the disclosure.

FIG. 2 illustrates a top view of a visual axis measurement system 200 in accordance with the disclosure. Visual axis measurement system 200 may include a visual axis measurement device 210 in combination with a near point target 212. More details of near point target 212 are described with reference to FIG. 3.

FIG. 2 also shows a pair of human eyes 214 that are positioned in close proximity to visual axis measurement device 210. The lines of site of human eyes 214 pass through visual axis measurement device 210 and are fixed upon near point target 212. Near point target 212 may be in a fixed and stationary position relative to visual axis measurement device 210. More specifically, near point target 212 may be in a fixed and stationary position at a typical reading distance, d1, from visual axis measurement device 210. A typical reading distance, d1, may be in the range of from about 300 mm to about 500 mm. In one example, the distance, d1, may be about 381 mm. Alternatively, near point target 212 may be handheld at the distance, d1, from visual axis measurement device 210.

A pair of slits (shown in FIGS. 4A and 4B) within visual axis measurement device 210 that are associated with human eyes 214 may be self-adjusted by the user of visual axis measurement system 200 (e.g., an optician's patient) until aligned with the patient's visual axes. In doing so, subjective patient feedback is utilized in determining the distance between his/her visual axes. This is in contrast to the long-standing and current practice of physically measuring the optical axes, which is an objective measurement that is often inaccurate. In doing so, visual axis measurement device 210 is utilized to measure accurately the distance between the visual axes of human eyes 214 for the purpose of determining accurately the position of a pair of bifocal lens segments (not shown) within a pair of eyeglass lenses (not shown). More details of visual axis measurement device 210 are described with reference to FIGS. 4A and 4B. More details of a method of using visual axis measurement system 200 are described with reference to FIGS. 5, 6A, and 6B.

Figure 3:
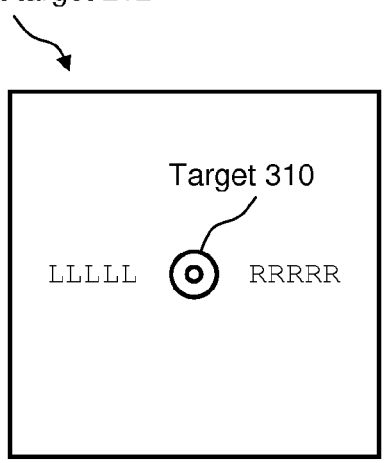
FIG. 3 illustrates a front view of a near point target of the visual axis measurement system of FIG. 2.

FIG. 3 illustrates a front view of near point target 212 of visual axis measurement system 200 of FIG. 2. Near point target 212 may be mechanism upon which a target 310 may be printed, affixed, or displayed. Near point target 212 may be formed of, for example, but not limited to, card stock paper or cardboard that is suitably rigid to stand with a support mechanism. In another example, near point target 212 may be a video display device, such as a computer display, for displaying target 310. Target 310 may be any image that is sized such that, at the distance, d1, of FIG. 2, its width spans the width of the slits (shown in FIGS. 4A and 4B) of visual axis measurement device 210, when visual axis measurement system 200 is in use. In one example, target 310 may be a set of concentric circles, as shown in FIG. 3. Additionally, target 310 may be surrounded by a set of characters, such as alpha/numeric characters, which are used as viewable offset indicators that provide indication of a relative fixation point away from target 310.

Figure 4A:
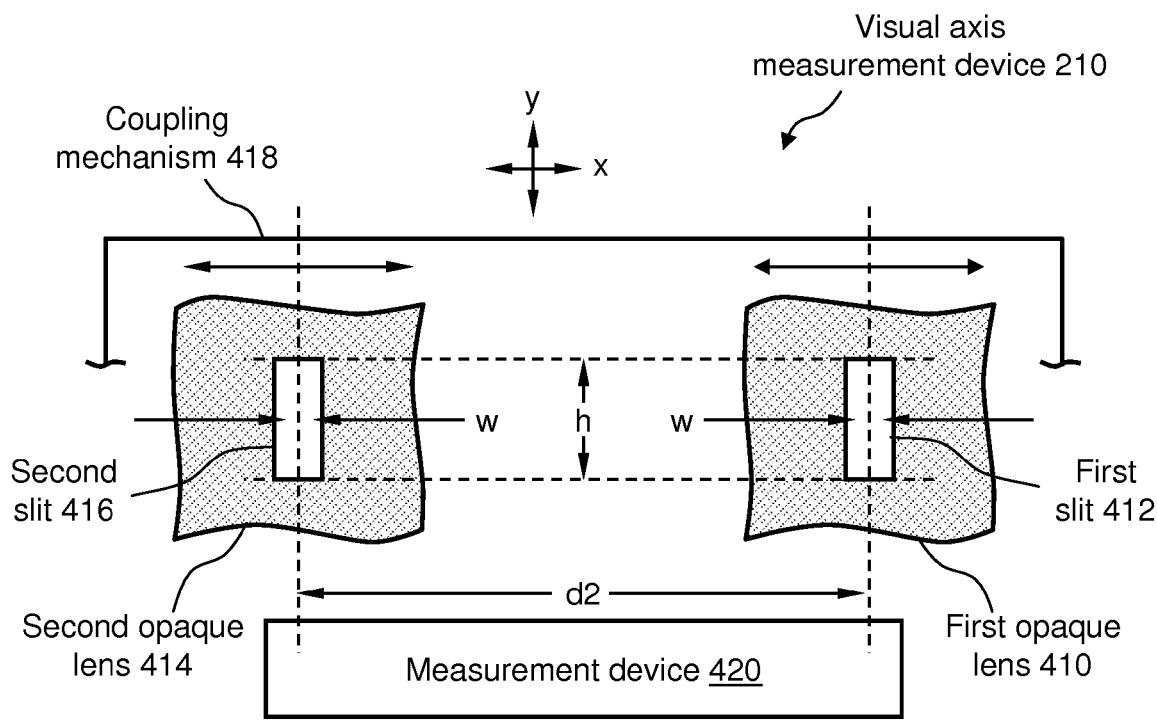
FIGS. 4A and 4B illustrate front views of a visual axis measurement device of the visual axis measurement system of FIG. 2.
Figure 4B:
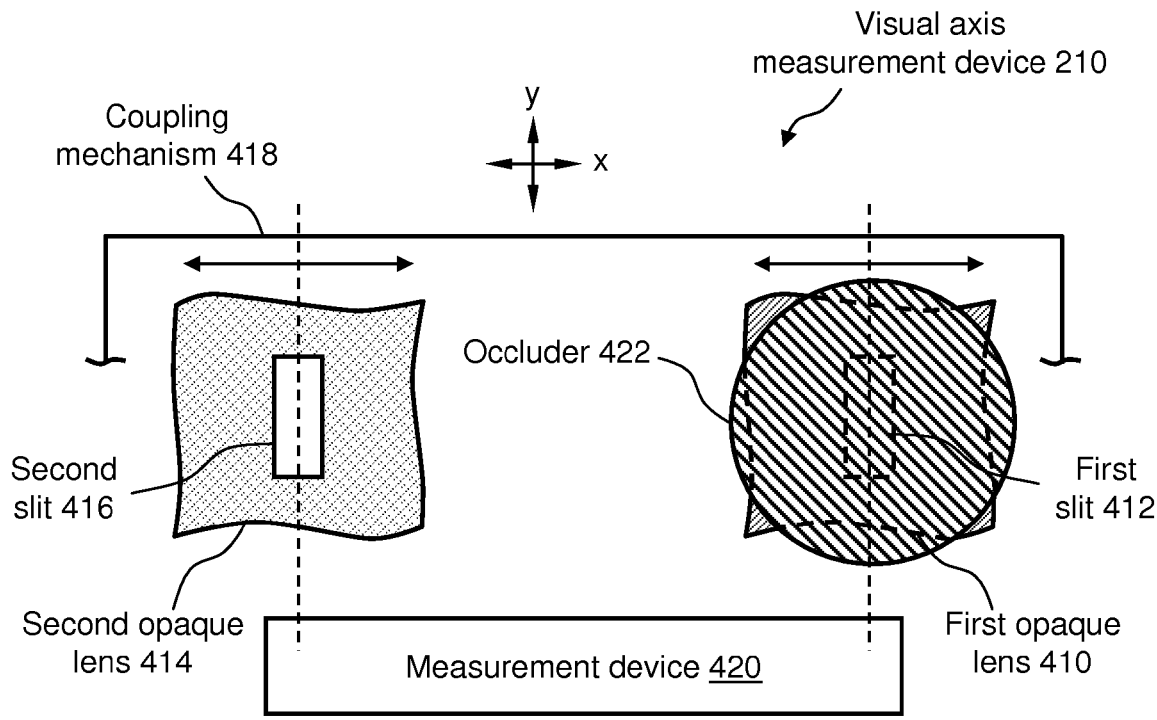

FIGS. 4A and 4B illustrate front views of visual axis measurement device 210 of visual axis measurement system 200 of FIG. 2. Visual axis measurement device 210 may be formed of a pair of opaque lenses, each having a slit therein, that are adjustably coupled one to another along an axis that runs between a patient's two eyes. More specifically, FIG. 4A shows that visual axis measurement device 210 may include a first opaque lens 410 within which is installed a first slit 412 and a second opaque lens 414 within which is installed a second slit 416. First opaque lens 410 and second opaque lens 414 are mechanically attached to a coupling mechanism 418. Additionally, visual axis measurement device 210 may include a measurement device 420 for measuring an adjustable distance, d2, between the centers of first slit 412 and second slit 416.

First opaque lens 410 and second opaque lens 414 may be formed of any lightweight, rigid, and nontransparent material, such as, but not limited to, nontransparent molded plastic. First opaque lens 410 and second opaque lens 414 may each be sized to approximate roughly the size of a human eye socket and to, at least, accommodate the size and geometry of first slit 412 and second slit 416, respectively. First slit 412 and second slit 416 may be openings within first opaque lens 410 and second opaque lens 414, respectively. A height, h, of first slit 412 and second slit 416 may be, for example, but not limited to, in the range of from about 20 mm to about 40 mm. In one example, the height, h, of first slit 412 and second slit 416 may be about 25 mm. A width, w, of first slit 412 and second slit 416 may be, for example, but not limited to, in the range of from about 0.01 mm to 3.0 mm.

Visual axis measurement device 210 may be a standalone device or a device that is integrated into other vision screening equipment. In one example, visual axis measurement device 210 may be a standalone device, such as a headrest apparatus into which a patient rests his/her chin in a manner that his/her eyes are in close proximity to first opaque lens 410 and second opaque lens 414 of visual axis measurement device 210.

Coupling mechanism 418 may be any mechanism to which first opaque lens 410 and second opaque lens 414 are mechanically coupled and by which the distance, d2, between first slit 412 and second slit 416 may be self-adjusted by the patient by adjusting first opaque lens 410 and/or second opaque lens 414 along an x-axis of coupling mechanism 418. In one example, coupling mechanism 418 may be a lead screw (not shown) that is coupled to either first opaque lens 410 or second opaque lens 414 or two lead screws (not shown) that are coupled to first opaque lens 410 or second opaque lens 414, respectively. One or more thumbwheel controls (not shown) of the one or more lead screws provides one or more self-adjustment mechanism for the patient. Alternatively, the lead screws may be motor driven under the control of the patient. In another example, coupling mechanism 418 may be an eyeglasses-type frame into which first opaque lens 410 or second opaque lens 414 may be slidably installed via a set of grooves or slots (not shown) running along the x-axis of coupling mechanism 418.

Coupling mechanism 418 may provide various levels of control. In one example, coupling mechanism 418 may provide independent control of both first opaque lens 410 and second opaque lens 414 along the x-axis. In another example, either first opaque lens 410 or second opaque lens 414 are held stationary while either first opaque lens 410 or second opaque lens 414 is adjustable along the x-axis of coupling mechanism 418. In another example, both first opaque lens 410 and second opaque lens 414 are simultaneously adjusted along the x-axis of coupling mechanism 418, such that the distance, d2, either narrows or widens. Additionally, coupling mechanism 418 may provide adjustability of first opaque lens 410 and second opaque lens 414 such that the distance, d2, is adjustable in a range of, for example, but not limited to, from about 40 millimeters (mm) to about 80 mm.

Measurement device 420 may be any commercially available manual or automated linear measuring device that is capable of measuring the full range of the distance, d2. In one example, measurement device 420 may be a Standard English ruler or a metric ruler. In another example, measurement device 420 may be a commercially available digital or manual caliper device. In another example, measurement device 420 may be a commercially available electronic linear measurement device, such as, but not limited to, Proscale model #701, that is mechanically and electrically integrated into visual axis measurement device 210 and that has a digital display for displaying automatically the distance, d2, between the centers of first slit 412 and second slit 416.

FIG. 4B shows additional details of visual axis measurement device 210. In particular, FIG. 4B shows that axis measurement device 210 may further include an occluder 422. Occluder 422 may be any mechanism for optionally blocking either first slit 412 and second slit 416. Occluder 422 may be formed of any lightweight, rigid, and nontransparent material, such as, but not limited to, nontransparent molded plastic. Occluder 422 may be a handheld device that may be moved manually between first opaque lens 410 and second opaque lens 414 by the patient. Alternatively, occluder 422 may be mechanically coupled to visual axis measurement device 210 (e.g., coupled to coupling mechanism 418) such that it may toggle between first opaque lens 410 and second opaque lens 414. Alternatively, two instances of occluder 422 may be included within visual axis measurement device 210, e.g., a first occluder 422 for first opaque lens 410 and a second occluder 422 for second opaque lens 414.

With continuing reference to FIGS. 2, 3, 4A, and 4B, the present disclosure provides a method of measuring accurately the visual axis of the patient's eyes in order to determine accurately the placement of bifocal lens segments within eyeglass lenses that includes, but is not limited to the high level steps of:
1. providing a near point target, such as near point target 212 of FIGS. 2 and 3, to the patient for viewing by use of visual axis measurement device 210;
2. providing an alignment mechanism, such as first opaque lens 410 that has first slit 412 and second opaque lens 414 that has second slit 416 of visual axis measurement device 210 of FIGS. 2, 4A, and 4B, which are adjustably coupled, for aligning first slit 412 and second slit 416 between the patient's eyes and near point target 212 and along the patient's visual axes; and
3. providing a measurement mechanism, such as measurement device 420 of visual axis measurement device 210, for measuring the distance, d2, between the centers of first slit 412 and second slit 416 and, thereby, determining the spacing between the visual axes of the patient's eyes. More details of a method of performing a visual axis alignment and measurement operation by use of visual axis measurement system 200 are provided with reference to FIG. 5.

Figure 5:
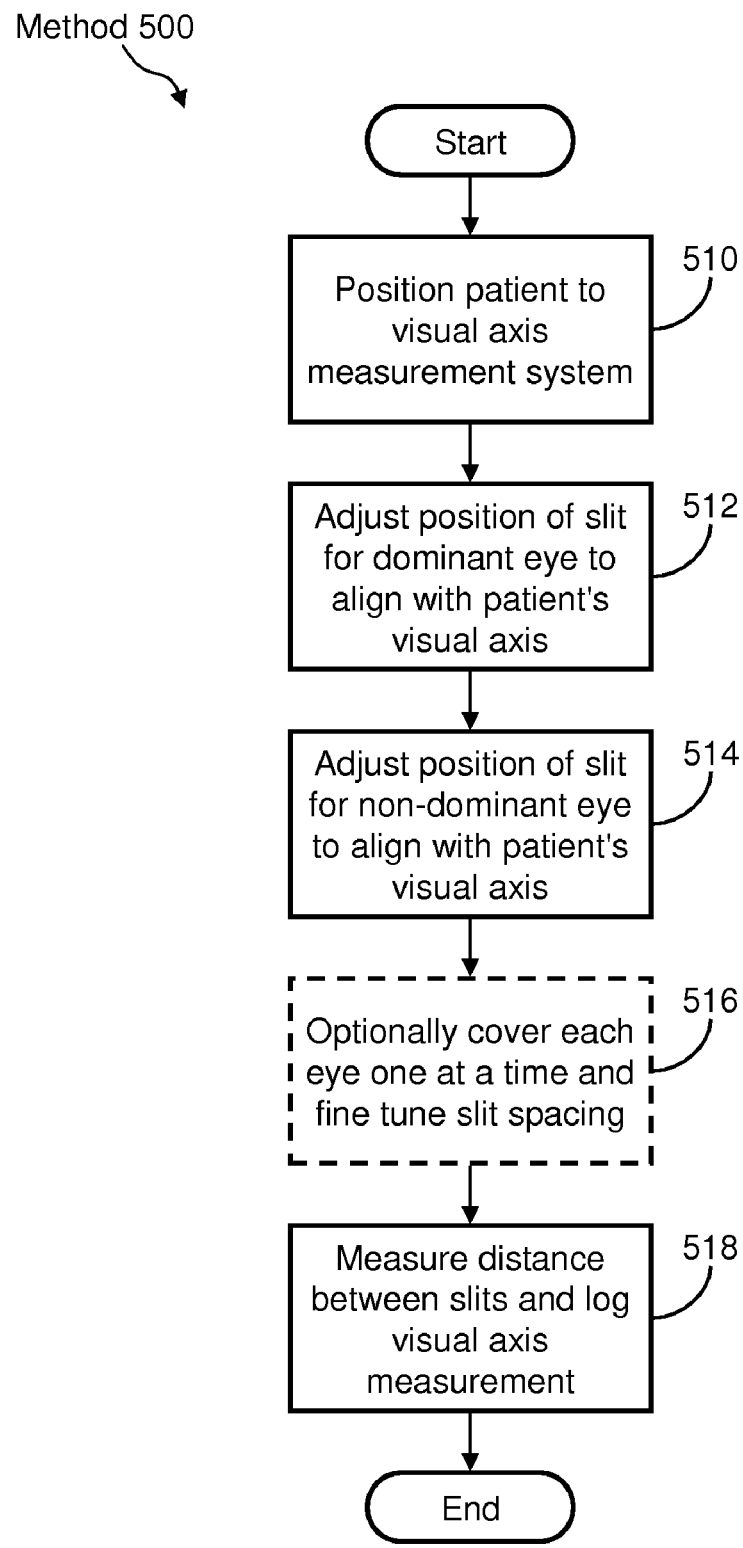
FIG. 5 illustrates a method of performing a visual axis alignment and measurement operation by use of the visual axis measurement system of FIG. 2.

FIG. 5 illustrates a method 500 of performing a visual axis alignment and measurement operation by use of a visual axis measurement system, such as visual axis measurement system 200 of FIG. 2. Method 500 includes, but is not limited to, the following steps.

At step 510, the patient is positioned at visual axis measurement system 200. More specifically, the patient is positioned at visual axis measurement device 210 of visual axis measurement system 200 such that his/her eyes are in close proximity to first opaque lens 410 and second opaque lens 414. Method 500 proceeds to step 512.

Figure 6A:
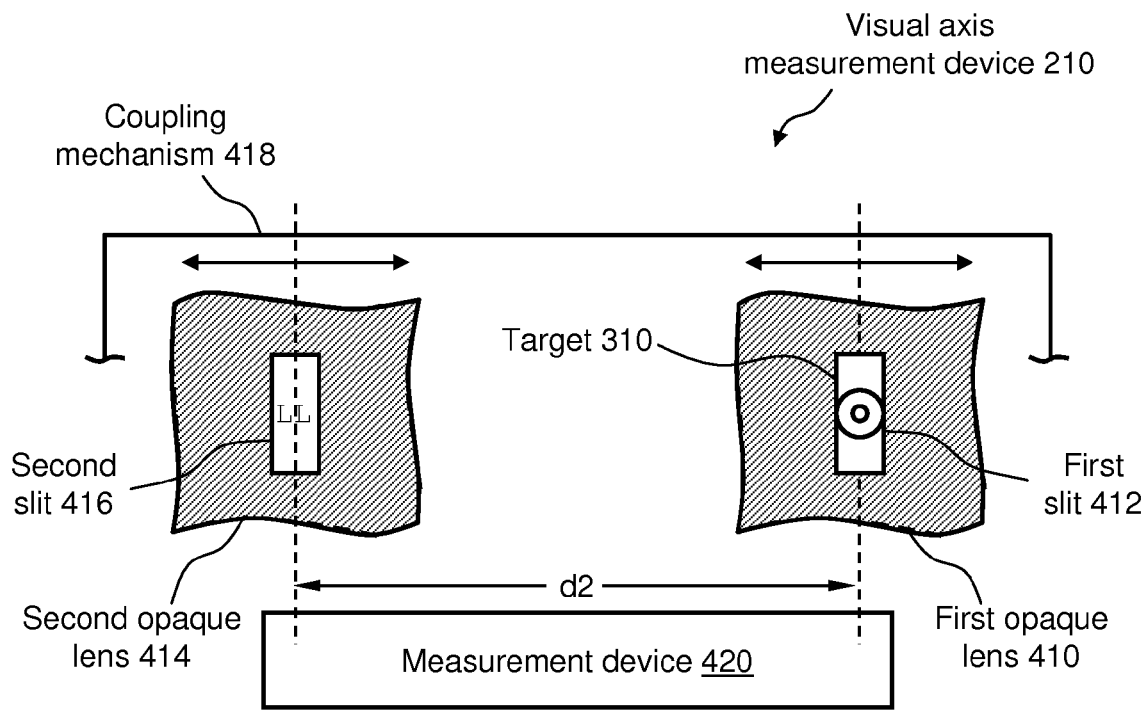
FIGS. 6A and 6B illustrate front views of the visual axis measurement device of the visual axis measurement system of FIG. 2 when in use.

At step 512, the position of the slit that is associated with the patient's dominant eye is adjusted by use of coupling mechanism 418 until target 310 of near point target 212 is centered within the slit as viewed by the patient, which is an indication that the position of the slit is aligned along the patient's visual axis. For example, if the patient's eye that is in close proximity to first opaque lens 410 is his/her dominant eye, the position of first opaque lens 410 is adjusted by use of coupling mechanism 418 until target 310 of near point target 212 is centered within first slit 412 as viewed by the patient, as illustrated in FIG. 6A. In doing so, first slit 412 is aligned with the visual axis of the patient's dominant eye when the patient's gaze is fixed upon target 310. FIG. 6A shows target 310 of near point target 212 centered within first slit 412 of first opaque lens 410, which is an indication that the position of first slit 412 is aligned along the patient's visual axis. FIG. 6A also shows that target 310 is not centered within second slit 416 of second opaque lens 414, which is an indication that the position of second slit 416 is not aligned along the patient's visual axis. FIG. 6A shows that target 310 of near point target 212 is sized to approximate the full width of first slit 412 and second slit 416 at the distance, d2, when aligned. Method 500 proceeds to step 514.

Figure 6B:
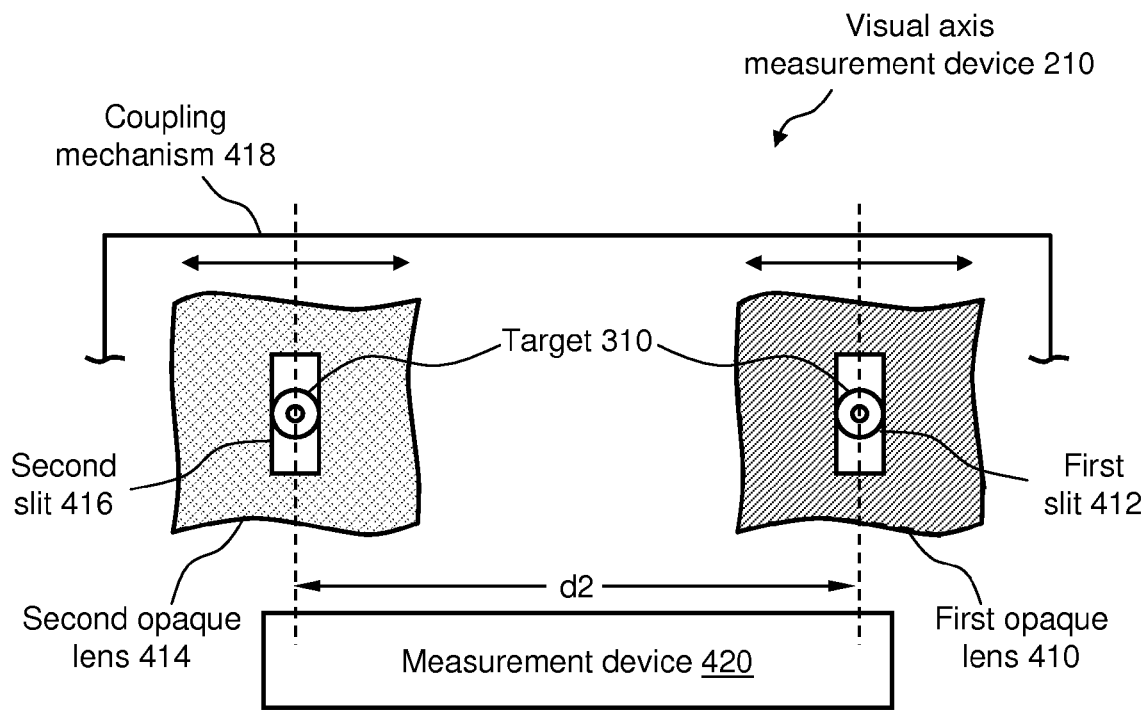

At step 514, the position of the slit that is associated with the patient's non-dominant eye is adjusted by use of coupling mechanism 418 until target 310 of near point target 212 is centered within the slit as viewed by the patient, which is an indication that the position of the slit is aligned along the patient's visual axis. For example, if the patient's eye that is in close proximity to second opaque lens 414 is his/her non-dominant eye, the position of second opaque lens 414 is adjusted by use of coupling mechanism 418 until target 310 of near point target 212 is centered within second slit 416 as viewed by the patient, as illustrated in FIG. 6B. In doing so, second slit 416 is aligned with the visual axis of the patient's non-dominant eye when the patient's gaze is fixed upon target 310. FIG. 6B shows target 310 of near point target 212 centered within second slit 416 of second opaque lens 414 along with target 310 centered within first slit 412 of first opaque lens 410, which is an indication that the position of second slit 416 is aligned along the patient's visual axis. Method 500 proceeds to step 516.

At optional step 516, the patient may cover each eye one at a time and fine tune the slit spacing. More specifically, the patient may first cover second slit 416 of second opaque lens 414 with occluder 422, leaving target 310 of near point target 212 visible to the patient within first slit 412 of first opaque lens 410 only. The patient may then fine tune the position of first slit 412 of first opaque lens 410 by use of coupling mechanism 418 until target 310 is yet better centered within first slit 412. Subsequently, the patient removes occluder 422 from blocking second slit 416 of second opaque lens 414. The patient may then cover first slit 412 of first opaque lens 410 with occluder 422, as shown in FIG. 4B, leaving target 310 of near point target 212 visible to the patient within second slit 416 of second opaque lens 414 only. The patient may then fine tune the position of second slit 416 of second opaque lens 414 by use of coupling mechanism 418 until target 310 is yet better centered within second slit 416. In doing so, first slit 412 and second slit 416 are yet better aligned along their respective visual axis. Method 500 proceeds to step 518.

At step 518, the distance between the slits is measured and the visual axis measurement is logged. More specifically, the distance, d2, between the centers of first slit 412 and second slit 416 is measured by use of measurement device 420 and logged in the patient's records. This visual axis measurement represents the distance between the visual axes of the patient's right and left eyes when gazing in a reading position and is an accurate measurement of the proper placement of the bifocal segments within the patient's eyeglass lenses. This is illustrated with reference to FIG. 7.

Figure 7:
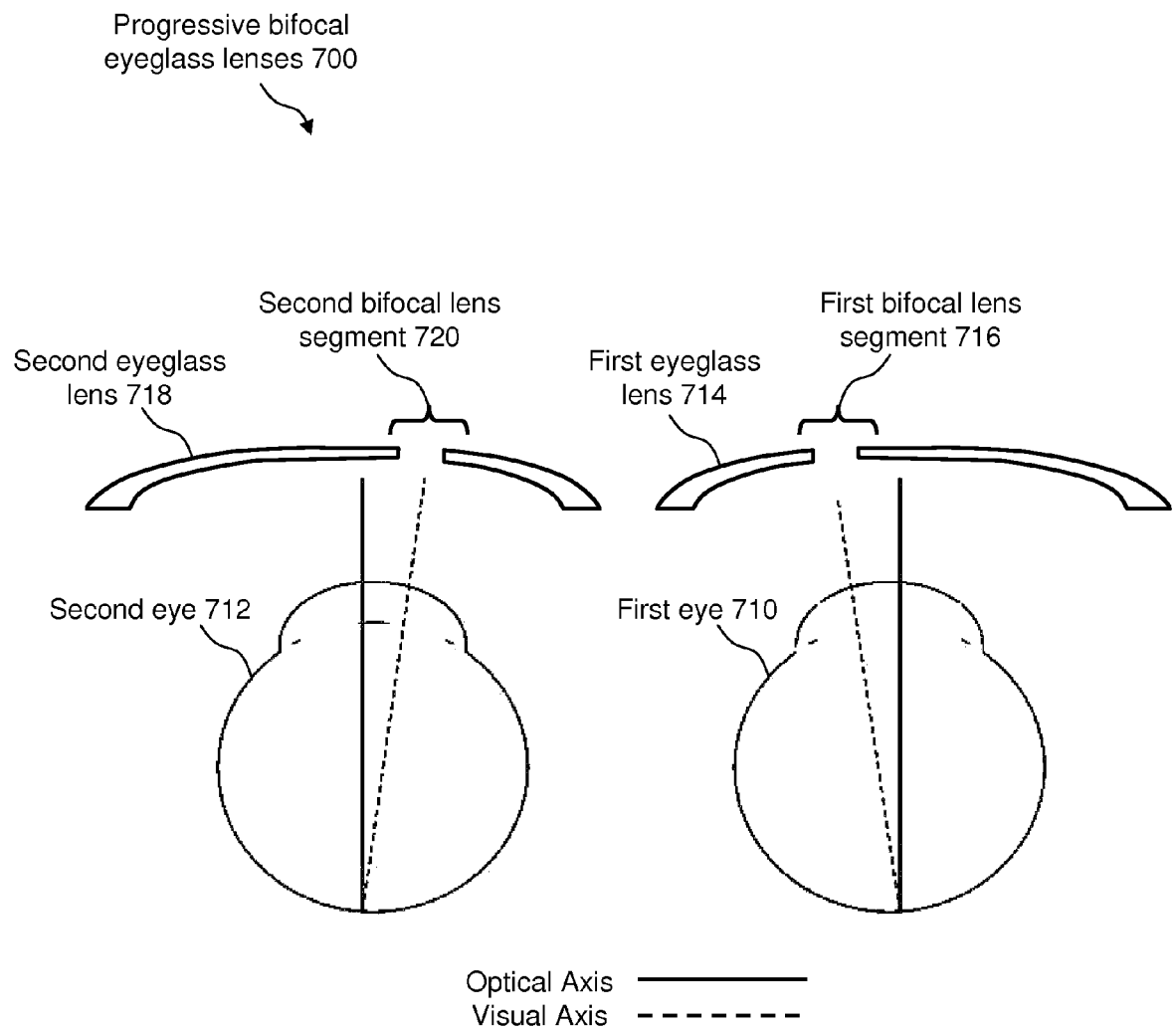
FIG. 7 illustrates a cross-sectional view of a pair of progressive bifocal eyeglass lenses, which result from the use of the visual axis measurement system of FIG. 2.

In particular, FIG. 7 illustrates a cross-sectional view of a pair of progressive bifocal eyeglass lenses 700, which result from the use of visual axis measurement system 200 of FIG. 2. In particular, FIG. 7 shows a first eye 710, which may be a subject's right eye, that is directed toward a first eyeglass lens 714 of progressive bifocal eyeglass lenses 700. Integrated within first eyeglass lens 714 is a first bifocal lens segment 716, which is aligned physically with the visual axis of first eye 710. Similarly, FIG. 7 shows a second eye 712, which may be a subject's left eye that is directed toward a second eyeglass lens 718 of progressive bifocal eyeglass lenses 700. Integrated within second eyeglass lens 718 is a second bifocal lens segment 720, which is aligned physically with the visual axis of second eye 712. FIG. 7 illustrates the placement of first bifocal lens segment 716 and second bifocal lens segment 720 based on the steps of method 500, which uses visual axis measurement system 200 of the present disclosure. Because the placement of first bifocal lens segment 716 and second bifocal lens segment 720 are aligned with the patient's visual axes, instead of with the patient's optical axes, the patient sees clearly (e.g., no blurriness or degradation of the perceived binocular image) when reading with his/her progressive bifocal lenses.

An exemplary embodiment has been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A visual axis and alignment measurement system, comprising:
   a. a visual axis measurement device; and
   b. a visual target, said visual target positioned at a distance (d1) from, and in visual contact with, said visual axis measurement device,
   wherein, said visual axis measurement device, comprises:
      first and second opaque lens adjustably coupled to one another along an axis that runs between a patient's two eyes;
      first and second slits defined within said first and second opaque lens respectively; and
      a coupling mechanism mechanically attached to said first and second opaque lens, wherein said coupling mechanism is used to adjust a distance (d2) between said first and second slits.

2. The visual axis and alignment measurement system of claim 1, further comprising a measurement device, wherein said measurement device measures said distance (d2) between centers of said first and second slits.

3. The visual axis and alignment measurement system of claim 2, wherein said measurement device comprises a standard English or metric ruler.

4. The visual axis and alignment measurement system of claim 2, wherein said measurement device comprises a caliper device.

5. The visual axis and alignment measurement system of claim 2, wherein said measurement device comprises a electronic linear measurement device mechanically and electrically integrated into said visual axis measurement device.

6. The visual axis and alignment measurement system of claim 1, further comprising an occluder, wherein said occluder occludes said first and/or second slit.

7. The occluder of claim 6, wherein said occluder is mechanically coupled to said visual axis measurement device.

8. The visual axis and alignment measurement system of claim 1, wherein said distance (d1) is in a range of from about 300 mm to about 500 mm.

9. The visual axis and alignment measurement system of claim 1, wherein width (w) or said first and second slits is in a range of from about 0.01 mm to 3.0 mm.

10. The visual axis and alignment measurement system of claim 1, wherein height (h) of said first and second slits is in a range of from about 20 mm to about 40 mm.

11. The visual axis and alignment measurement system of claim 1, wherein said distance (d2) between the centers of said first and second slits is in a range of from about 40 millimeters to about 80 millimeters.

12. The visual axis and alignment measurement system of claim 1, wherein said visual target is a printed display.

13. The visual axis and alignment measurement system of claim 1, wherein said visual target is a video display device.

14. A method of performing a visual axis alignment and measurement, comprising the steps of:
   a. positioning a patient at a visual axis measurement device wherein, said visual axis measurement device, comprises:
      first and second opaque lens adjustably coupled to one another along an axis that runs between a patient's two eyes;
      first and second slits defined within said first and second opaque lens respectively; and
      a coupling mechanism mechanically attached to said first and second opaque lens, wherein said coupling mechanism is used to adjust a distance (d2) between said first and second slits;
   b. adjusting said first or second slit that is associated with said patient's dominant eye, such that a visual target at a distance (d1) is aligned with said patient's dominant eye's visual axis;
   c. adjusting said first or second slit that is associated with said patient's non-dominant eye, such that a visual target, at a distance (d1), is aligned with said patient's nondominant eye's visual axis; and
   d. measuring distance (d2) between centers of said first and second slit, wherein said distance (d2) is a visual axis measurement.

15. The method of performing a visual axis alignment and measurement of claim 9, further including after step (c) the step of alternatively covering each of said patient's eyes with an occluder and time tuning first and second slit adjustment.

16. A progressive bifocal eyeglass lens, comprising:
an eyeglass lens, comprising a bifocal lens segment integrated into said eyeglass lens
wherein, said bifocal lens segment is physically aligned with a visual axis of a patient's eye as a result of using a visual axis and alignment measurement system and method, the visual axis and alignment measurement system, comprising: a visual axis measurement device; and a visual target, the visual target positioned at a distance (d1) from, and in visual contact with, the visual axis measurement device, wherein, said visual axis measurement device, comprises: first and second opaque lens adjustably coupled to one another along an axis that runs between a patient's two eyes; first and second slits defined within said first and second opaque lens respectively; and a coupling mechanism mechanically attached to said first and second opaque lens, wherein said coupling mechanism is used to adjust a distance (d2) between said first and second slits.

* * * * *